United States Patent
Roscher

Patent Number: 5,576,454
Date of Patent: Nov. 19, 1996

[54] PROCESS FOR PREPARING ALKANEPHOSPHONIC ANHYDRIDES

[75] Inventor: Günter Roscher, Kelkheim, Germany

[73] Assignee: Hoechst AG, Germany

[21] Appl. No.: 331,128

[22] Filed: Oct. 28, 1994

[30] Foreign Application Priority Data

Oct. 30, 1993 [DE] Germany .................. 43 37 190.6

[51] Int. Cl.⁶ .................................................. C07F 9/02
[52] U.S. Cl. ................................... 558/386; 562/878
[58] Field of Search ................. 562/878; 558/303, 558/386; 560/55

[56] References Cited

U.S. PATENT DOCUMENTS 4,267,125  5/1981  Dürsch et al. .

FOREIGN PATENT DOCUMENTS 0002733  7/1979  European Pat. Off. .
0015483  9/1980  European Pat. Off. .
 979282  1/1965  United Kingdom .

*Primary Examiner*—Joseph Conrad
*Attorney, Agent, or Firm*—Connolly & Hutz

[57] ABSTRACT

Process for preparing phosphonic anhydrides of the formula (I)

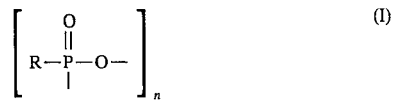

in which R is $(C_1-C_{10})$-alkyl which is unsubstituted or substituted by alkyl groups, alkoxy groups, fluorine, chlorine or bromine atoms, nitro groups, cyano groups, trifluoromethyl groups, phenyl groups, it being possible for the phenyl radical in turn to carry alkyl groups, alkoxy groups, fluorine, chlorine, bromine atoms, nitro groups, cyano groups or alkoxycarbonyl groups, and $n \geq 3$, by reacting a phosphonic acid of the formula (II)

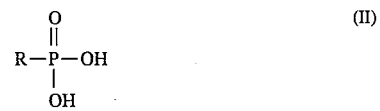

in which R has the meaning given, with diketene, if appropriate at elevated temperature.

16 Claims, No Drawings

PROCESS FOR PREPARING ALKANEPHOSPHONIC ANHYDRIDES

The present invention relates to a process for preparing alkanephosphonic anhydrides.

Alkanephosphonic anhydrides, such as, for example, propanephosphonic anhydride, are valuable intermediates. They are used, for example, for preparing flame retardants, for protecting metals against corrosion, for complexing metals, for linking peptides or else as crosslinking agents for polymers.

Various methods for preparing alkanephosphonic anhydrides are known. In general, the starting material is the corresponding alkanephosphonic acid. This acid can be converted to the phosphonic dichloride using, for example, phosphorus trichloride, thionyl chloride or phosgene (DE-A 2,225,545). The alkanephosphonic dichloride can be reacted either with alkanephosphonic acid or else a stoichiometric amount of water to give the alkanephosphonic anhydride (EP 154 83), with simultaneous formation of hydrogen chloride. Another known method is transanhydridization of alkanephosphonic acid with, for example, acetic anhydride (DE-A 2,758,580). This involves heating a mixture of alkanephosphonic acid and acetic anhydride under reflux and continuously distilling off the acetic acid formed. The methods involving the chloride route give rise to technical difficulties which are caused by the formation of hydrogen chloride.

The transanhydridization reaction of alkanephosphonic acids is very time-consuming since the acetic acid formed has to be distilled off in order to reach the equilibrium, as a result of which the space-time yields are low. Due to the fact that the reaction usually requires excess acetic anhydride, the reaction volume required is several times that of the alkanephosphonic anhydride recovered.

Accordingly, there was a great need for developing a process which avoids the abovementioned disadvantages and can be put into practice without any great technical expenditure and moreover makes the desired phosphonic anhydride available in high yield without the formation of undesirable by-products.

This object is achieved by a process for preparing phosphonic anhydrides of the formula (I)

in which R is $(C_1-C_{10})$-alkyl which is unsubstituted or substituted by alkyl groups, alkoxy groups, fluorine, chlorine or bromine atoms, nitro groups, cyano groups, trifluoromethyl groups, phenyl groups, it being possible for the phenyl radical in turn to carry alkyl groups, alkoxy groups, fluorine, chlorine, bromine atoms, nitro groups, cyano groups or alkoxycarbonyl groups, and $n \geq 3$, which process comprises reacting a phosphonic acid of the formula (II)

in which R has the meaning given, with diketene, if appropriate at elevated temperature.

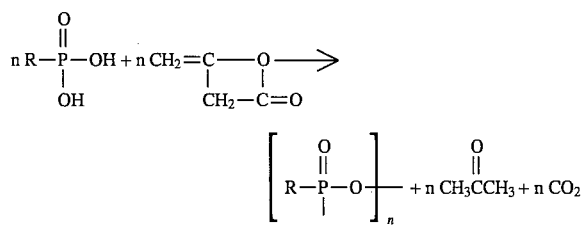

The particular advantage of this process is that the only by-products formed are $CO_2$ and acetone which are ecologically safe and easy to remove.

The process can be advantageously used for phosphonic anhydrides of the formula I in which R is $C_1$-$C_{10}$-alkyl or -alkenyl where n is at least 3, in particular 5–100. The process is also important for preparing ethanephosphonic anhydride, propanephosphonic anhydride, butanephosphonic anhydride, vinylphosphonic anhydride.

In many cases, carrying out the reaction at temperatures between 50° C. and 180° C., in particular 70° C. and 150° C., preferably 80° C. and 120° C., has given good results. It has proven advantageous to meter the diketene to the initial charge of alkanephosphonic acid. The diketene added reacts spontaneously, which can be seen from the stoichiometric amount of $CO_2$ formed and the amount of acetone distilling off. In general, a stoichiometric ratio of alkanephosphonic acid to diketene is used, a slight diketene excess being advantageous in many cases. It has proven advantageous to use 0.8 to 3 mol, in particular 0.9 to 2 mol, preferably 1 to 1.5 mol, of diketene per mole of phosphonic acid.

The examples which follow serve to illustrate the process without limiting it.

APPARATUS

Oil bath for temperature control, 5 l three-neck flask equipped with stirrer, dropping funnel, condenser, receiver, water scrubber for exhaust gas cleaning, gas meter for measuring exhaust gas NL is the amount of gas in liters, relative to standard conditions (0° C./1 atm).

EXAMPLE 1

The flask is charged with 3 kg of propanephosphonic acid. The internal temperature of the flask is adjusted to 120° C. 2400 g of diketene are added dropwise at a uniform rate from the dropping funnel over a period of 2 hours. As diketene addition begins, exhaust gas is formed behind the waste-water scrubber. About 5 minutes after diketene supply was started, distillate starts collecting in the receiver. The amount of exhaust gas equals the amount of diketene added dropwise in terms of moles.

Behind the exhaust gas scrubber a total of 640 NL of gas essentially comprising $CO_2$ are collected. 1080 g are obtained as distillate. The distillate contains >95% of acetone. At the bottom of the exhaust gas scrubber, an aqueous solution containing 350 g of acetone is formed.

The reaction residue, which is an amount of 2800 g, contains 8% of acetone, 82% of propanephosphonic anhydride and 10% of unconverted propanephosphonic acid.

EXAMPLE 2

The experimental conditions and amounts used are as in Example 1. However, the temperature in the reaction vessel is adjusted to 100° C.

If the amount of exhaust gas is to equal the amount of diketene added dropwise in terms of moles, the reaction must be carried out at a reduced rate of addition of the diketene. Uniform addition of diketene now requires 3½ hours.

The amount of exhaust gas formed is as in Example 1. 860 g of acetone are obtained as distillate, and the bottom of the exhaust gas scrubber contains 350 g of acetone. 3022 g remain as reaction residue containing 15% of acetone, 75% of propanephosphonic anhydride and 10% of unconverted propanephosphonic acid.

EXAMPLE 3

Experimental conditions and amounts used are as in Examples 1 and 2.

In the reaction vessel, the temperature is adjusted to 80° C.

If the equilibrium between the amount of gas and the amount of diketene supplied is to be reached, the rate of addition of the diketene must be reduced further. The reaction time required is now 5 hours. The amount of exhaust gas is as in Examples 1 and 2. The amount of the acetone distillate is 453 g, and the bottom of the exhaust gas scrubber contains 350 g of acetone. 3418 g remain as reaction residue containing 25% of acetone, 66% of propanephosphonic anhydride and 8% of propanephosphonic acid.

EXAMPLE 4

The experimental setup is as in Example 1. Instead of the 2400 g of diketene used in Example 1, only 2235 g of diketene are metered in at a uniform rate over a period of 2 hours.

The amount of exhaust gas is 590 NL, the amount of acetone distillate is 993 g, and the bottom of the water scrubber contains 325 g of acetone.

2820 g of the following composition: acetone 8%, propanephosphonic anhydride 76%, propanephosphonic acid 15% remain as the bottom product of the reaction.

EXAMPLE 5

The experimental setup is as in Example 1. Instead of the 2400 g of diketene used in Example 1, only 2040 g of diketene are metered in at a uniform rate over a period of 2 hours. The amount of exhaust gas is 540 NL. 885 g of acetone distillate are formed, and the bottom of the water scrubber contains 298 g of acetone.

2840 g of the following composition: acetone 8%, propanephosphonic anhydride 73%, propanephosphonic acid 18% remain as the bottom product of the reaction.

What is claimed is:

1. A process for preparing phosphonic anhydrides of the formula (I)

in which R is $(C_1-C_{10})$-alkenyl, $(C_1-C_{10})$-alkyl which is unsubstituted or substituted by alkyl groups, alkoxy groups, fluorine, chlorine or bromine atoms, nitro groups, cyano groups, trifluoromethyl groups, unsubstituted or substituted phenyl groups, wherein said substituents for the phenyl groups are alkoxy groups, fluorine, chlorine, bromine atoms, nitro groups, cyano groups or alkoxycarbonyl groups, and $n \geq 3$ and less than or equal to 100, which process comprises reacting a phosphonic acid of the formula (II)

in which R has the meaning given, with diketene, a temperature of between 50° and 180° C.

2. The process as claimed in claim 1, in which R is $C_1-C_{10}$ -alkyl or -alkenyl, and n is 3 to 100.

3. The process as claimed in claim 1, wherein the alkanephosphonic acid is introduced first and the diketene is metered in.

4. The process as claimed in claim 1, wherein 0.8 to 3 mol of diketene are used per mole of phosphonic acid.

5. The process as claimed in claim 4, wherein 0.9 to 2 mol of diketene are used per mole of phosphonic acid.

6. The process as claimed in claim 4, wherein 1 to 1.5 mol of diketene are used per mole of phosphonic acid.

7. The process as claimed in claim 4, wherein R is ethyl, propyl, butyl or vinyl, and n is 5 to 100.

8. The process as claimed in claim 7, wherein the reaction is carried out at a temperature between 80° C. and 120° C. and 1 to 1.5 mole of diketene are used per mole of phosphonic acid.

9. The process as claimed in claim 8, wherein the alkanephosphonic acid is introduced first and diketene is metered in.

10. The process as claimed in claim 9, wherein said anhydrides of formula (I) are ethanephosphonic anhydride, propanephosphonic anhydride, butanephosphonic anhydride or vinylphosphonic anhydride.

11. The process as claimed in claim 10, wherein said anhydrides of formula (I) are propanephosphonic anhydride produced in an amount from 66% to 82%.

12. The process as claimed in claim 10, wherein said anhydrides of formula (I) are propanephosphonic anhydride produced in an amount from 73% to 82%.

13. The process as claimed in claim 1, wherein the temperature is between 70° C. and 150° C.

14. The process as claimed in claim 13, wherein the temperature is between 80° C. and 120° C.

15. The process as claimed in claim 1, wherein said anhydrides of formula (I) are ethanephosphonic anhydride, propanephosphonic anhydride, butanephosphonic anhydride or vinylphosphonic anhydride.

16. The process as claimed in claim 1, wherein said anhydrides of formula (I) are produced in an amount from 66% to 82%.

* * * * *